(12) United States Patent
Moulin

(10) Patent No.: US 9,326,882 B2
(45) Date of Patent: May 3, 2016

(54) RETAINING FABRIC HAVING POCKETS

(75) Inventor: Herve Moulin, Saint Etienne (FR)

(73) Assignee: BERTHEAS & CIE, Saint Chamond (FR)

( * ) Notice: Subject to any disclaimer, the term of this patent is extended or adjusted under 35 U.S.C. 154(b) by 2115 days.

(21) Appl. No.: 10/599,197

(22) PCT Filed: Mar. 11, 2005

(86) PCT No.: PCT/FR2005/050156
§ 371 (c)(1),
(2), (4) Date: Aug. 13, 2008

(87) PCT Pub. No.: WO2005/092238
PCT Pub. Date: Oct. 6, 2005

(65) Prior Publication Data
US 2008/0294081 A1 Nov. 27, 2008

(30) Foreign Application Priority Data
Mar. 22, 2004 (FR) ..................................... 04 50564

(51) Int. Cl.
A61F 5/02 (2006.01)
D03D 11/02 (2006.01)

(52) U.S. Cl.
CPC ................ A61F 5/028 (2013.01); D03D 11/02 (2013.01)

(58) Field of Classification Search
USPC ............. 602/19, 18, 20, 27, 5, 64, 16, 21, 23, 602/26; 128/876, 898; 2/309, 311, 338, 2/162, 163, 170, 16
See application file for complete search history.

(56) References Cited

U.S. PATENT DOCUMENTS

| | | | |
|---|---|---|---|
| 1,243,230 A | 10/1917 | Smith | |
| 1,389,525 A | 8/1921 | Mosby | |
| 1,496,578 A | 6/1924 | Kops | |
| 2,301,047 A | 11/1942 | Hendley | |
| 2,614,261 A | 10/1952 | McTighe | |
| 2,651,302 A | 9/1953 | Berry | |
| 2,655,916 A | 10/1953 | Timmins | |
| 2,677,868 A | 5/1954 | Banneyer | |
| 2,753,864 A | 7/1956 | Weidemann, Jr. | |
| 2,921,456 A * | 1/1960 | Evans | 66/176 |
| 2,957,475 A | 10/1960 | Drake | |
| 5,070,866 A | 12/1991 | Alexander et al. | |
| 5,188,586 A * | 2/1993 | Castel et al. | 602/19 |
| 5,902,757 A * | 5/1999 | Stern et al. | 442/324 |
| 7,022,095 B2 * | 4/2006 | Schneider | 602/64 |
| 7,074,202 B1 * | 7/2006 | Weber et al. | 602/20 |

* cited by examiner

Primary Examiner — Ophelia A Hawthorne
(74) Attorney, Agent, or Firm — Heslin Rothenberg Farley & Mesiti P.C.; Victor A. Cardona, Esq.

(57) ABSTRACT

A support fabric with pockets for accommodating stiffener comprises two woven layers which are joined by stitch bonding and, during production, are separated from one another in areas so that they are not joined in these areas, thereby directly defining one or more profiled pockets to accommodate stiffener inserted in the pockets after production. The pockets are incorporated inside the body of the support fabric. Each pocket has an opening for inserting one of the stiffener.

4 Claims, 2 Drawing Sheets

RETAINING FABRIC HAVING POCKETS

CROSS REFERENCE TO RELATED APPLICATIONS

This application is a 371 filing of International Application PCT/FR2005/050156 filed Mar. 11, 2005, and published as International Publication No. WO 2005/092238 A2, in French, on Oct. 6, 2005, and claims priority of French Application No. 0450564, filed on Mar. 22, 2004, which applications are hereby incorporated by reference herein in their entirety.

BACKGROUND ART

The invention relates to the technical field of making orthoses and supports for medical, sporting and protective purposes in particular.

The inventive approach adopted by the applicant was inspired by the problems encountered with lumbar support belts.

Textile-based belts of this type are known and are designed with stiffening means of the metal stay type or sheets separately fitted in the support fabric.

Figure 1:
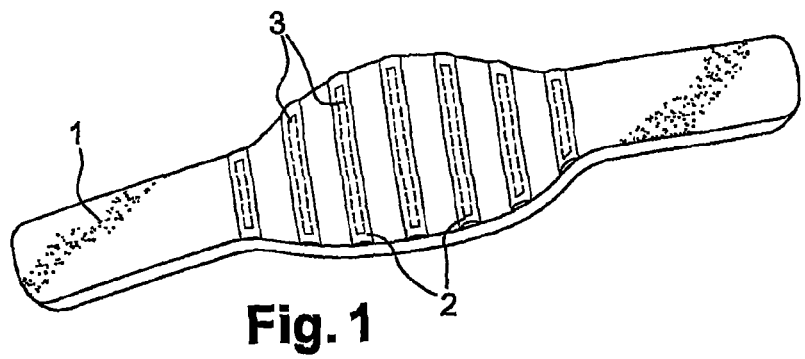

FIG. 1 shows a belt according to the prior art. It is denoted by (1) and its middle part which corresponds to application of pressure to the individual's back comprises a plurality of stay covers (2) that are separately fitted and stitched or otherwise attached to one of the surfaces of the belt. These stay covers which are closed, after fitting the stays (3), are generally made of a material that is different to the material which the belt is made of, for example materials such as woven tape, artificial leather or certain types of plastic. In practice, these stay covers are obtained from a flat strip which, when the belt is made, is separately fitted on the belt by appliqué in order to form pockets for accommodating stays. These stay covers, in the form of flat strips, are thus separately fitted and attached by stitching or similar methods to the support fabric, the stay being sandwiched between the body of the fabric and said strip. The pockets thus formed are permanently arranged with predetermined spacing. Depending how they are produced, belts may have additional pockets located in the part that is an extension of the part that is applied to the back so that it extends onto the flanks of the individual wearing the belt. Thus, belts are produced and designed specifically for predetermined sizes and with a predefined number within a range depending on the age, size and morphology of the wearer.

In practice, this type of belt which is widely adopted by many manufacturers has several drawbacks or limitations.

A first drawback is firstly the fact that it is expensive to produce because it is necessary to make the actual textile belt and the pockets separately. Stiffening means are then inserted into said pockets which are then closed and subsequently, or simultaneously, attached to the belt by stitching or other means of attachment. Alternatively, depending on the manufacturing technique, the pockets can be arranged on the belt open at appropriate locations and then the operator inserts the stays one by one and this operation is continued by closing all the pockets. This job therefore takes a long time and involves many different operations. In addition, the problem of positioning the pockets on the belt requires inspection, marking out and perfect measurement of distances in order to fit a plurality of pockets that accommodate said stiffening means.

Another drawback is the non-modifiable use of pockets on the belt so that even though there may be several belt sizes, the belt that is offered to the wearer is not always perfectly appropriate to the user's morphology.

Another drawback is the fact that the volume of the belt thus designed is considerable because the pockets for accommodating stays protrude on one side and the belt, when rolled up for storage or packing, takes up a considerable space.

Another drawback resulting from the technique used to produce these belts is the fact that they often have a single predefined application.

Despite these drawbacks or limitations, these belts are, in the absence of other solutions and suggestions, used in accordance with this concept.

BRIEF SUMMARY OF THE INVENTION

The applicant's approach was therefore to rethink the concept of the support fabric so as to allow, during the production of belts or other appliances, firstly a reduction in manufacturing costs but also the prospect of a wider range of design options.

Also, the applicant wanted to propose a support fabric that can be more easily customized to suit the user's morphology and his or her needs.

In other words, the applicant reflected on the design of a support fabric that makes it possible, by using a new production technique, to insert and fit means offering a larger range of applications for medical, sporting and protective applications, besides the original application of the lumbar support belt type.

Research carried out by the applicant resulted in it designing a new type of support fabric that overcomes all the problems stated and allows a substantial reduction in manufacturing costs.

Thus, according to a first aspect of the invention, the support fabric provided with pockets for accommodating, in particular, stiffening means is distinctive in that it comprises two woven layers which are joined by stitch bonding and, during production, are separated from one another in areas so that they are not joined whereby directly defining one or more profiled pockets and being able to accommodate one or more of the means that are inserted after production and in that said pocket(s) is/are incorporated inside the body of the support fabric, and each pocket has an opening for inserting one of the means.

According to another aspect of the invention, said means inserted into the support fabric are stiffeners of the stay or other type.

According to another aspect of the invention, said means inserted into the support fabric have a therapeutic and/or comfort function.

According to another aspect of the invention, the method for producing the support fabric is characterized in that it involves producing two woven layers that are superimposed and attached by stitch bonding in order to form unitary parts of the support fabric and then, in a predetermined cycle, separating said layers a given distance apart and then moving them together and joining them again in order to successively form one or more profiled pockets for subsequently inserting and accommodating external means and in that, during production of the support fabric, said pocket(s) is/are partially closed by leaving an insertion opening to fit said above-mentioned means.

According to another aspect of the manufacturing method, selvedges are established, one of the selvedges being closed over the entire length of the support fabric and the other selvedge being partially closed apart from in the pocket area in order to allow insertion of said means into said pockets.

BRIEF DESCRIPTION OF THE DRAWING FIGURES

These aspects and others will become apparent from the following description.

Figure 2:
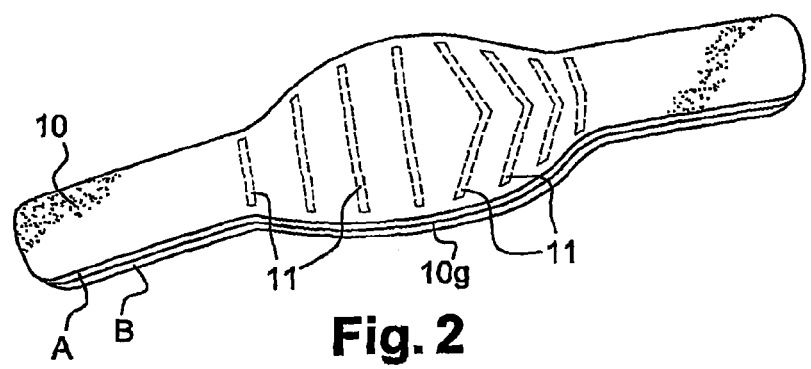
Figure 3:
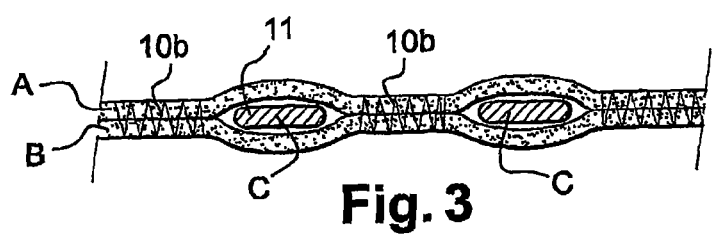
Figure 4:
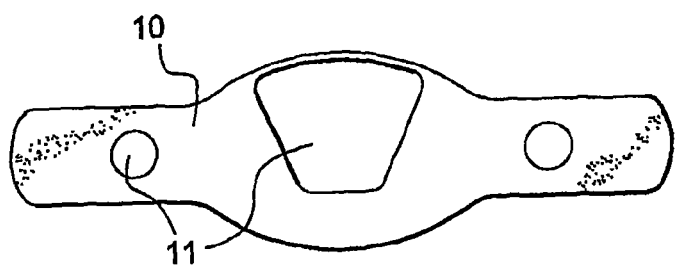
Figures 5A, 5B, 5C:
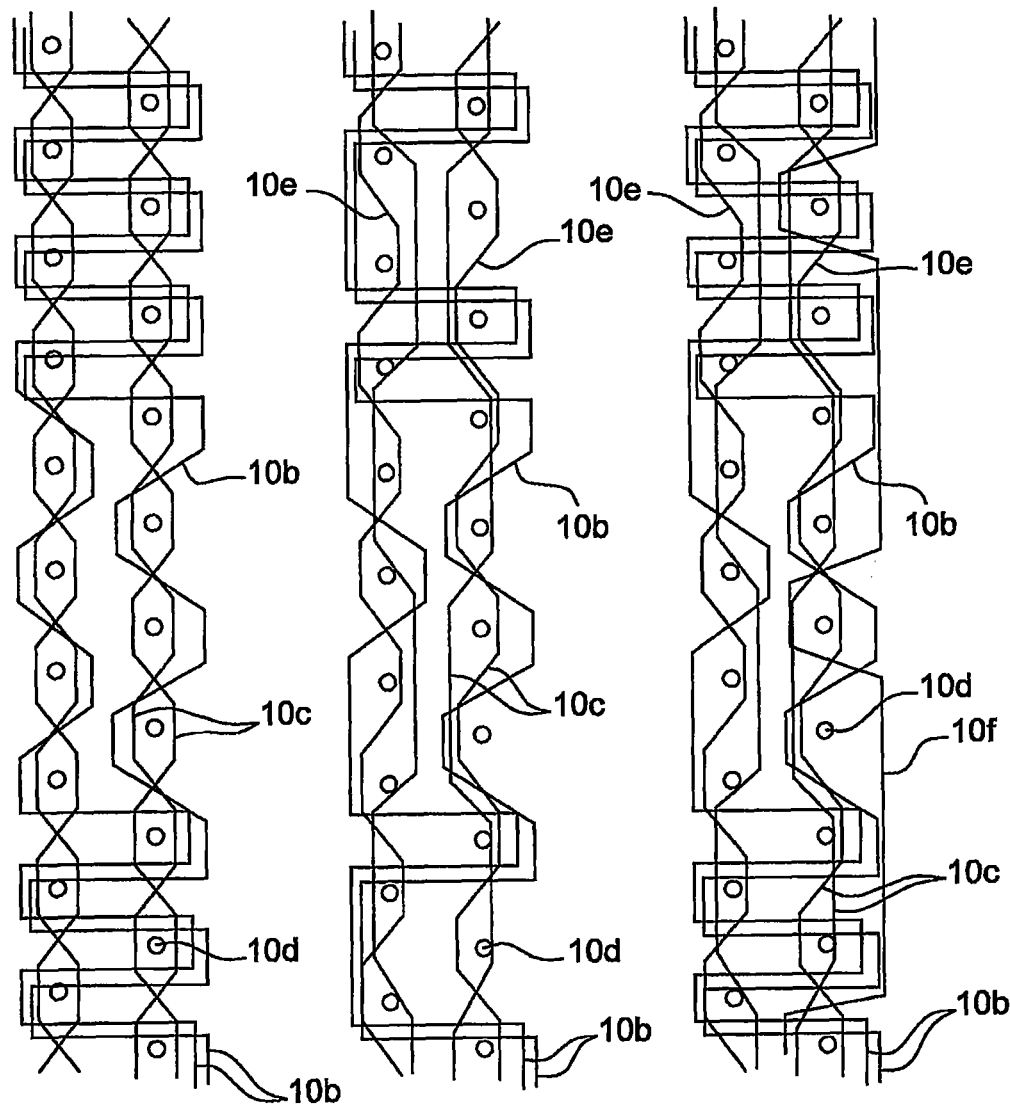

The object of the invention is illustrated in a non-limitative fashion, reference being made to the Figures in which:

FIG. 1 is a perspective view of a lumbar support belt according to the prior art, FIG. 2 is a perspective view of a first embodiment of the support fabric according to the invention, FIG. 3 is a large-scale partial sectional view showing the support fabric according to the invention with pockets arranged at regular intervals for accommodating stiffening means of the stay type, FIG. 4 is a schematic plan view of a support fabric according to the invention designed with pockets over the width of the fabric for accommodating therapeutic and/or comfort means such as pads made of silicone or other materials, FIGS. 5A, 5B, 5C are non-limitative examples showing the production of pockets on a support fabric with various alternative shapes and spacings.

DETAILED DESCRIPTION

In order that the present invention may more readily be understood, the following description is given, merely by way of example, reference being made to the accompanying drawings.

The support fabric according to the invention is denoted by (10) in its entirety. It is made from two superimposed woven layers (A-B) which can have any known thread count and weave with warp threads and weft threads in any possible configuration with elasticity over all or part of the woven layers.

These two woven layers (A-B) are, according to the invention, joined to each other during weaving by stitch bonding (10b), the threads being totally integrated into all the warp threads operating at a predetermined pitch depending on the pocket or pockets (C) to be produced.

Thus, according to the invention, the support fabric forms, at certain locations inside the body of the support fabric, profiled pockets corresponding to the non stitch-bonded areas of the two woven layers (A-B). In practice, at the location where the above-mentioned pockets are to be formed, the bonding stitches (10b) are deflected and routed differently over the so-called woven layers in accordance with a predetermined pitch that corresponds to the dimensions and the configuration of the pocket(s) to be obtained, then said bonding stitches are deflected again so as to resume their initial trajectory inside the body of the two woven layers, after forming the pocket, in order to ensure their stitch bonding function. The pockets (C) are thus defined by the space or volume between the two woven layers (A-B) which can move apart from each other since they are not bonded at the location(s) in question. The pockets are delimited by the work of the bonding stitches integrated into the two woven layers immediately before and after their deflection or trajectory as stated above.

Thus, according to the invention, said support fabric according to the invention is continuously produced in a single operation on the loom by means of known mechanisms. The number of pockets thus created over the length of the support fabric depends on the desired application of the support fabric—whether it is a support belt, for example, or has other uses. It will also be easy to program automatic operation of the loom in order to make the support fabric with the desired number of pockets, respective spacing and width depending on the nature and characteristics of means (11) that are inserted, such as stays or other means. In addition, the length of the accommodating pockets can extend over the entire width of the support fabric or over part of its width. To achieve this, it is sufficient to adapt the trajectory of the bonding stitches in accordance with the chosen programming. According to the invention, the means fitted in the pockets which may have a stiffening function in the form of stays are totally integrated inside the body of the support fabric, leaving the woven parts of the woven layers exposed and giving a new design and specific external appearance to the support fabric.

In addition, one of the advantages of the invention is that it is possible to produce a support fabric according to the method of the invention, but only fit a small number of stays or other means compared with the number of pockets, thus allowing production of the belt or other appliances to be adapted depending on the wearer's needs and/or morphology. In other words, one can vary the number of stays or other means and their distribution in the support fabric because said stays or other means can be accessed by opening the corresponding pockets. Said pocket openings may remain open or be closed by stitching or other means.

The selvedges (10g) are established, one being closed over the entire length of the support fabric and the other selvedge being partially closed apart from in the area of the pockets in order to allow insertion of said means into said pockets.

Use of the invention using the above-mentioned manufacturing method makes it possible to produce pockets inside the body of the support fabric in order to fit stiffening means in the form of stays but also sheets as well as means having other uses such as pads, thermoformed material, gel bags, diffusion pockets and others. FIG. 4 schematically shows, by way of example, various pocket configurations that can have an identical or different geometrical configuration in order to accommodate identical or different means (11).

The configuration of the pockets can be established during production, including non-straight shapes or with chevrons for example, but also geometrical shapes that correspond to the shapes of the means and components to be retained, it being crucial to provide an appropriate opening for each pocket in order to insert said means. To achieve this, said pocket openings may open out close to or along one selvedge of the support fabric but may also open out over the width of the support fabric.

Thus, the method according to the invention offers many possible applications for medical, sporting, protective, therapeutic and/or comfort applications in particular.

FIGS. 5A, 5B, 5C show examples of weaves and the formation of pockets by way of example only. The warp threads are identified by (10c), the weft threads are identified by (10d), the bonding threads are identified by (10b), the elastic threads are identified by (10e) and any backing threads are identified by (10f).

The advantages of the invention are evident. The new design of the support fabric by defining, during production, pockets for accommodating external means and components, thereby substantially reducing subsequent manufacturing costs, is emphasized. The diverse applications of these support fabrics and the possibility of adapting them to real needs are also underlined.

By way of information, support fabrics with pockets according to the invention can be used to make medical belts for lumbar support, post-surgery or abdominal belts, orthoses, splints, strapping etc.

Use of the invention therefore opens up an extremely wide range of possible uses under optimum economic conditions.

Finally, the existing openings of the pockets can remain open or allow removal or fitting of said means (11) at any time or they can be closed by any means, thus allowing a high degree of modularity and versatility.

The invention claimed is:

1. A support fabric provided with pockets for accommodating stiffening means, comprising:
    a first woven layer and a second woven layer formed by a plurality of threads and joined to each other by bonding threads of the threads along a length of the support fabric;
    a plurality of pocket areas configured to receive one or more of the stiffening means;
    a plurality of non-pocket areas located between the pocket areas;
    said first woven layer comprising first bonding threads and said second woven layer comprising second bonding threads, a first bonding thread of said first threads extending from said first woven layer into said second woven layer in a first non-pocket area of said plurality of non-pocket areas and returning to said first woven layer in a second non-pocket area of said plurality of non-pocket areas, a second bonding thread of said second threads extending from said second woven layer into said first woven layer in said first non-pocket area and returning to said second woven layer in said second non-pocket area such that said first woven layer and said second woven layer are continuously joined to each other by stitch bonding in said first said first non-pocket area- and said second non-pocket area;
    said first woven layer and said second woven layer separated from each other in said plurality of pocket areas such that interior surfaces of said first woven layer and said second woven layer bound a cavity for receiving the stiffening means, said first bonding thread located in said second woven layer in a first pocket area of said plurality of pocket areas located between said first non-pocket area and said second non-pocket area and said second bonding thread located in said first woven layer in said first pocket area, each pocket area of said plurality of pocket areas having an opening for inserting one of the stiffening means.

2. The support fabric as claimed in claim 1, wherein said stiffening means comprises stiffeners of the stay type.

3. The support fabric as claimed in claim 1, wherein said stiffening means have at least one of a therapeutic and comfort function.

4. A support fabric provided with pockets for accommodating stiffening means, comprising:
    a first woven layer and a second woven layer joined to each other by bonding threads along a length of the support fabric;
    a plurality of pocket areas configured to receive one or more of the stiffening means;
    a plurality of non-pocket areas located between the pocket areas;
    said first woven layer and said second woven layer separated from each other in said plurality of pocket areas such that interior surfaces of said first woven layer and said second woven layer bound a cavity for receiving the stiffening means, each pocket of said plurality of pockets having an opening for inserting one of the stiffening means; and
    wherein said first woven layer comprises first threads and said second woven layer comprises second threads, and at least one of said first threads extending into said second woven layer and back into said first layer and at least one of said second threads extending into said first woven layer and back into said second layer to join said first woven layer and said second woven layer to each other.

* * * * *